United States Patent [19]

Chiodini et al.

[11] Patent Number: 5,153,272

[45] Date of Patent: Oct. 6, 1992

[54] CURABLE MIXES OF FLUOROELASTOMERS CONTAINING BORMINE OR IODINE AND OF ORGANIC PEROXIDES

[75] Inventors: Graziella Chiodini, Saronno; Attilio LaGostina, Spinetta Marengo; Michele Merenda, Frugarolo; Anna Minutillo, Milan; Ezio Montessoro, Spinetta Marengo, all of Italy

[73] Assignee: Ausimont S.r.l., Milan, Italy

[21] Appl. No.: 555,636

[22] Filed: Jul. 23, 1990

[30] Foreign Application Priority Data

Jul. 24, 1989 [IT] Italy .................. 21277 A/89

[51] Int. Cl.⁵ .................. C08C 19/04; C08F 8/00
[52] U.S. Cl. .................. 525/345; 525/326.3; 525/375; 525/387
[58] Field of Search ............ 525/387, 326.3, 345, 525/375

[56] References Cited

U.S. PATENT DOCUMENTS

| | | |
|---|---|---|
| 2,916,481 | 12/1959 | Gilmont . |
| 2,965,619 | 12/1960 | Honn et al. ............ 525/387 |
| 2,999,854 | 9/1961 | Honn et al. ............ 525/387 |
| 3,129,204 | 4/1964 | Gilmont . |
| 3,135,805 | 6/1964 | Gilmont . |
| 3,299,019 | 1/1967 | Kealy ................ 525/387 |
| 3,419,577 | 12/1968 | Bieckert et al. ......... 525/387 |
| 3,449,191 | 6/1969 | Taylor ................ 525/387 |
| 3,654,216 | 4/1972 | Murray ................ 525/387 |
| 4,035,565 | 7/1977 | Apotheker et al. ....... 525/387 |
| 4,214,060 | 7/1980 | Apotheker et al. ....... 525/387 |
| 4,501,869 | 2/1985 | Tatemoto et al. ........ 525/387 |
| 4,831,085 | 5/1989 | Okabe et al. ........... 525/387 |
| 4,866,137 | 9/1989 | Pagliari et al. ........ 525/387 |

FOREIGN PATENT DOCUMENTS

| | | |
|---|---|---|
| 553191 | 2/1958 | Canada ................ 525/387 |
| 0208353 | 1/1987 | European Pat. Off. ...... 525/387 |
| 1208487 | 1/1966 | Fed. Rep. of Germany .... 525/387 |
| 3925743 | 2/1990 | Fed. Rep. of Germany . |
| 838963 | 6/1960 | United Kingdom ......... 525/387 |
| 1028235 | 5/1966 | United Kingdom ......... 525/387 |

OTHER PUBLICATIONS

Hawley's Condensed Chemical Dictionary-Eleventh Edition-p. 133.

Primary Examiner—Joseph L. Schofer
Assistant Examiner—N. Sarofin
Attorney, Agent, or Firm—Stevens, Davis, Miller & Mosher

[57] ABSTRACT

There are described mixes, which are curable by using radical intermediates, are based on fluoroelastomers containing bromine or iodine, exhibit, during curing, a low emission of toxic vapors of methyl bromide or iodide and are characterized in that they contain, as cross-linking agents, peroxides having the following formulas:

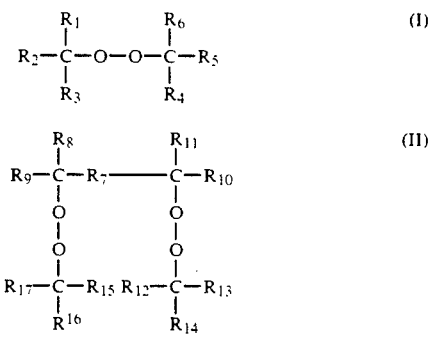

wherein the substituents from $R_1$ to $R_{17}$ have the significances defined in the specification.

8 Claims, No Drawings

CURABLE MIXES OF FLUOROELASTOMERS CONTAINING BORMINE OR IODINE AND OF ORGANIC PEROXIDES

BACKGROUND OF THE INVENTION

The present invention relates to mixes based on fluoroelastomers containing Br or J, additioned with particular organic peroxides, which exhibit, during curing, a low emission of toxic vapors of methyl bromide or iodide.

The cure with organic peroxides of the fluoroelastomers containing, as cure sites, bromine or iodine atoms along the polymeric chain and/or at the end of said chain is broadly known.

In such fluoroelastomers, bromine or iodine are introduced into the elastomer macromolecule by using, during the polymerization step, brominated or iodidated comonomers such as, in particular, fluorobrominated olefins, brominated or iodidated fluorovinyl ethers or by using, in the polymerization itself, brominated or iodidated compounds as chain transfers.

In the peroxide cure of said elastomers there are utilized, in general, organic peroxides of the aliphatic type, either saturated or unsaturated, such as e.g.: 2,5-dimethyl-2,5-di(ter.butylperoxy)hexine-3 2,5-dimethyl-2,5-di(-ter.butylperoxy)hexane, which give rise, in the curing process, to the formation of methyl radicals. These radicals, by combination with bromine or iodine contained in the fluoroelastomer, form methyl bromide or iodide, which are highly toxic volatile products and, as regards iodide, also a cancerogenous product.

Therefore, while the peroxide curing of fluoroelastomers containing Br or I permits to obtain cured articles having improved stability to steam and to other aggressive agents as compared with the articles obtained through a ionic curing, it is apparent, on the other hand, that said peroxide curing involves a serious hazard for the health of the operators entrusted with the processing of said elastomers.

Furthermore, it is not possible to avoid the drawback caused by said harmful emissions merely by using peroxides which do not release at all or release only little amounts of methyl radicals during their decomposition, because said peroxides could not cure at all or only weakly cure said fluoroelastomers. That is apparent, for example, when using organic perketalic peroxide of formula:

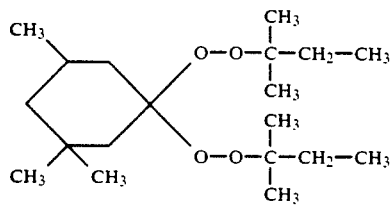

which, by decomposition, prevailingly provides ethyl radicals and only little amounts of methyl radicals, but which is not capable of curing the fluoroelastomers containing bromine or iodine.

DISCLOSURE OF THE INVENTION

Thus, it is an object of the present invention to substantially reduce or to eliminate the harmful emissions of methyl bromide or iodide, which occur during the radical curing, of fluoroelastomers containing Br or I, without, however, modifying the good rheological properties of the vulcanizate.

It has now been found that it is possible to substantially reduce the formation of the above-said toxic products by using particular organic peroxides, not only without jeopardizing the cure trend and results, but, conversely, improving the cure rate and the cross-linking yield.

It has furthermore been found that it is possible to further reduce or eliminate the methyl bromide or iodide emission if, in combination with said particular peroxides, little amounts of organic additives, to be specified hereinafter, are utilized.

By consequence, the object of the present invention is represented by curable mixes based on fluoroelastomers containing bromine and/or iodine in the polymeric chain, which comprise organic peroxides as radical cross-linking agents, and are characterized in that the peroxides are selected from the monoperoxides of formula:

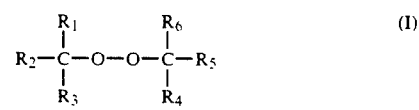

wherein:

$R_1$, $R_6$, like or different from each other, are $C_2$–$C_4$ alkyls;

$R_3$, $R_4$, like or different from each other are $C_1$–$C_4$ alkyls;

$R_2$, $R_5$, like or different from each other, are $C_1$–$C_4$ alkyls, phenyls, phenyls substituted by $C_1$–$C_4$ alkyls;

and the bisperoxides of formula:

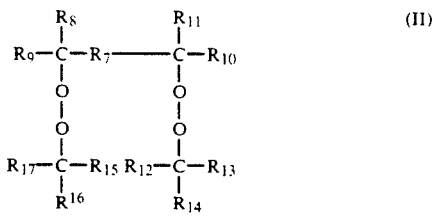

wherein $R_7$ is $C_1$–$C_6$ alkylene, $C_2$–$C_6$ alkenylene, $C_2$–$C_6$ alkynylene, phenylene;

$R_8$, $R_9$, $R_{10}$, $R_{11}$, like or different from one another, are $C_1$–$C_3$ alkyls;

$R_{13}$, $R_{15}$, like or different from each other, are $C_1$–$C_4$ alkyls;

$R_{12}$, $R_{14}$, $R_{16}$, $R_{17}$, like or different from one another, are $C_1$–$C_4$ alkyls;

provided that, when $R_7$ is phenylene, $R_8$, $R_{11}$, like or different from each other, are $C_2$–$C_4$ alkyls.

A further object of the present invention is curable positions based on fluoroelastomers containing Br and/or I, which comprise, besides the peroxides of formula (I) and/or (II), also little amounts, generally ranging from 0.1 to 1 part by weight for 100 parts of rubber (p.h.r.) of benzothiazole and derivatives thereof, preferably 2-mercaptobenzothiazole and its salts, in particular zinc salts, mercaptobenzothiazole disulphide (MBTS), morpholine-2-benzothiazole-sulphenamide, of 0.1–2 p.h.r. of N-phenyl maleimide (NPM) or derivatives thereof.

By the further use of little amounts of benzothiazole or its derivatives it is possible to obtain a complete suppression, during curing, of the methylene bromide and/or iodide, while retaining the good character of the vulcanizate prepared by using the peroxides of formula (I) and/or (II), with the additional advantage due to the increase of the time required by scorching to occur (scorching time), what results in a higher processing safety without affecting the cross-linking rate.

As fluoroelastomers containing bromine or iodine atoms as cure sites it is possible to cite, for example, the $CH_2=CF_2$ copolymers with $CF_3—CF=CF_2$ and, optionally, also with $C_2F_4$, and the $C_2F_4$ copolymers with perfluorovinylethers, containing little amounts of bromine or iodine, which are introduced by copolymerizing a little amount of brominated or iodidated monomer as the brominated olefins, the perfluorobromoalkyl-perfluorovinylethers, or also by the use of chain transfers, consisting of bromoalkyl or iodoalkyl compounds.

The peroxides of formula (I) or (II) are known in part, while in part they have been originally synthesized as the peroxides:

bis(1,1-diethylpropyl) peroxide (S 173);
bis(1-ethyl-1-methylpropyl) peroxide (S 176);
1,1-diethylpropyl,1-ethyl-1-methylpropyl-peroxide (S 185);
2,5-dimethyl-2,5-di-ter.amylperoxy-hexane (S 179);
which form a further object of the present invention.

The amounts of peroxides of formula (I) or (II), which are contained in the mixes according to the present invention, generally range from 1 part to 6 parts by weight for 100 parts of elastomer (p.h.r.) and in particular from 1.5 to 3 p.h.r.

Said peroxides, besides substantially reducing the emission of toxic methyl bromide and/or iodide by at least 90% and, in a few cases, by more than 95%, permit to obtain the following advantages:

increase by 20% to 150% in the cross-linking rate at 180° C.,
in a few cases, increase in the cross-linking yield at 180° C.,
improvement in the detach of the article from the mold.

The peroxides can be also utilized in the preparation of mixes carried on inert fillers, such as e.g. calcium carbonate or silica or mixtures thereof, which makes easier the utilization thereof and permits to avoid the drawbacks caused by their volatility.

The mixes based on fluoroelastomers containing bromine and/or iodine according to the present invention, comprise, besides organic peroxide and, optionally, benzothiazole, derivatives thereof or N-phenylmaleimide, the conventional ingredients utilized in the curable mixes, such as carbon black and other reinforcing fillers, peroxide curing coagents (for example triallyl isocyanurate), metal oxides and hydroxides (for example PbO, ZnO), and processing aids.

The following examples are given merely to illustrate and not to limit the present invention.

EXAMPLES 1–15

Tests were carried out to determine the $CH_3Br$ emissions of mixes containing the peroxides according to the invention and in some cases also mercaptobenzothiazole disulphide (MBTS), or N-phenylmaleimide (NPM) in comparison with the mixes containing conventional peroxide 2,5-dimethyl-2,5-di-ter.butylperoxy-hexane (Luperco 101 XL). The tested mixes were all based on terpolymer P.1, i.e. a terpolymer composed for 66.2% by moles of $CH_2=CF_2$, for 18.2% by moles of $C_3F_6$, for 15.2% by moles of $C_2F_4$ and containing bromoperfluorovinylether in amounts equal to 0.65% by weight of bromine. The ingredients of the mixes, besides the peroxides and the additives of the types and in the amounts indicated in Table 1, were the following:

4 p.h.r. of triallylisocyanurate (TAIC) at 75% on an inert filler,
3 p.h.r. of PbO,
30 p.h.r. of carbon black MT.

the $CH_3Br$ emissions during the curing step were determined according to the following modalities:

20 g of finely mixed particles (polymer + fillers) were treated at 180° C. in a closed reactor for 30 minutes at a pressure of 0.5 kg/cm² abs. in a $N_2$ atmosphere.

At the end, the whole was cooled to 40°–50° C. and, as an internal standard, 1 cc of A 114 ($C_2Cl_2F_4$, b.p. = 4° C.) was added.

The gas phase was mixed and then it was analyzed in a gas-chromatograph.
Column: POROPAK Q
Temperature: 100° C.

The cure trend was evaluated by determining the Δ torque (MH-ML) by means of the oscillating disk rheometer (ODR) (Monsanto type), according to standard ASTM D 2084/81, with "arc±3".

Table 1 shows the results of such determinations, where the $CH_3Br$ emissions are expressed as percent reduction of the standard emission of a mix containing the conventional peroxide Luperco 101XL (Example 1).

TABLE 1

| EX. | PEROXIDE | phr | ADDITIVE phr | TORQUE MH-ML | MAX | REDUCTION IN % OF EMISSION $CH_3Br$ |
|---|---|---|---|---|---|---|
| 1 | Luperco 101 XL *carried for 45% | 3 | — | 67 | 0.79 | — |
| 2 | S. 172 | 1.6 | — | 65 | 0.71 | 95 |
| 3 | S. 172 | 1.8 | — | 66 | 0.74 | 94 |
| 4 | S. 172 | 2.0 | — | 74 | 1.05 | 96 |
| 5 | S. 172 | 1.8 | MBTS 0.25 | 71 | 0.87 | 100 |
| 6 | S. 172 | 1.8 | NPM 1.5 | 75 | 1.01 | 98 |
| 7 | S. 172 - *carried for 40% | 4.5 | — | 69 | 0.78 | 96 |
| 8 | S. 172 - *carried for 40% | 4.5 | MBTS 0.25 | 66 | 0.66 | 100 |
| 9 | S. 173 | 1.3 | — | 50 | 1.08 | 95 |
| 10 | S. 176 - *carried for 40% | 5.1 | — | 66 | 1.15 | 95 |
| 11 | S. 176 - *carried for 40% | 6.8 | — | 68 | 1.24 | 95 |
| 12 | S. 176 - *carried for 40% | 8.5 | — | 68 | 1.37 | 94 |
| 13 | S. 176 - *carried for 40% | 8.5 | MBTS 0.25 | 73 | 1.60 | 100 |
| 14 | S. 179 | 1.5 | — | 70 | 0.95 | 95 |

TABLE 1-continued

| EX. | PEROXIDE | ADDITIVE phr | TORQUE phr | MH-ML | MAX | REDUCTION IN % OF EMISSION CH₃Br |
|---|---|---|---|---|---|---|
| 15 | S. 185 | 2.6 | — | 60 | 1.3 | 98 |

*carried on CaCO₃/SiO₂ 1:1

EXAMPLE 16

Curing tests in mold were carried out to determine the actual reduction, under real conditions, of the CH₃Br emissions by subjecting to gas-chromatographic analysis, under the conditions indicated in the preceding examples, an air sample drawn above the molded article immediately after the detach of the vulcanizate from the mold.

comparison with standard mixes, which contain Luperco 101XL as a peroxide.

In particular, Table 2 indicates the compositions of the tested mixes and their characteristics.

Table 3 shows the percentages of reduction of the CH₃Br emissions and a few characteristic values, which are indicative of the cure trend.

Table 4 indicates the characteristics of the cured material.

TABLE 2

| | COMPOSITION OF THE MIX (ASTM D. 3182-82) | | | | | | ASTM D. 1646-82 | | |
|---|---|---|---|---|---|---|---|---|---|
| | | | | | | | 135° C. MOONEY SCORCH | | 121°C. MOONEY |
| Mix No. | polymer | peroxide | phr | TAIC | PbO | carbon black | MV | t 15 | ML (1' + 10') |
| 1 | P. 1 | LUPERCO 101 XL 45% | 3.0 | 4 | 3 | 30 | 48 | 13' 36" | 103 |
| 2 | P. 1 | PEROXIMON S172 PURE (1) | 1.8 | 4 | 3 | 30 | 48 | 10' 55" | 103 |
| 3 | P. 40 | LUPERCO 101 XL 45% | 3.0 | 4 | 3 | 30 | 12 | 26' 30" | 33 |
| 4 | P. 40 | PEROXIMON S172 PURE (1) | 1.8 | 4 | 3 | 30 | 17 | 20' 30" | 42 |

(1) = bis(1,1-dimethylpropyl)peroxide.

TABLE 3

| | | CURING CHARACTERISTICS (ASTM 02084-81 - ODR. 180° C.; arc +/−3) | | | | | | | |
|---|---|---|---|---|---|---|---|---|---|
| POLYMER | MIX No. (from tab. 2) | ML (lbf · in) | MH (lbf · in) | ts 2 (s) | t'50 (s) | t'90 (s) | V max (lbf · in/s) | Δ TORQUE MH-ML | REDUCTION IN % OF CH₃Br EMISSION |
| P. 1 | 1 | 22 | 80 | 72 | 126 | 360 | 0.58 | 58 | — |
| P. 1 | 2 | 22 | 86 | 66 | 123 | 294 | 0.70 | 64 | 92% |
| P. 40 | 3 | 4 | 51 | 78 | — | 399 | 0.40 | 47 | — |
| P. 40 | 4 | 6 | 55 | 75 | — | 270 | 0.60 | 49 | 96% |

TABLE 4

| | | MECHANICAL PROPERTIES | | | | | | | | | | |
|---|---|---|---|---|---|---|---|---|---|---|---|---|
| | | after press-cure (170° C. + 10') | | | | | after post-cure (250° C. + 24 h) | | | | | |
| | | ASTM D. 412-83 Tensile propert. | | | | ASTM D. 2240-8 Hardness | ASTM D. 412-83 Tensile properties | | | | ASTM D2240-81 Hardness | ASTM D1414-78 (*) |
| POLYMER | MIX No. (from tab. 2) | (MPa) M100 | (MPa) M200 | (MPa) T.S. | (%) E.B. | (points) H-Shore A | (MPa) M100 | (MPa) M200 | (MPa) T.S. | (%) E.B. | (points) H-Shore A | C.S. (%) O-R 214 |
| P. 1 | 1 | 3.7 | 9.1 | 12 | 284 | 72 | 5.6 | 15.9 | 18.2 | 233 | 75 | 33 |
| P. 1 | 2 | 4.4 | 11.7 | 14 | 257 | 73 | 6.0 | 17.7 | 21.2 | 231 | 73 | 25 |
| P. 40 | 3 | 2.4 | 5.1 | 6.4 | 383 | 66 | 4.0 | 10.0 | 13.4 | 262 | 70 | 44 |
| P. 40 | 4 | 3.0 | 6.3 | 7.4 | 339 | 68 | 4.4 | 11.2 | 14.3 | 252 | 71 | 45 |

(*) C.S. = compression set at 200° C. for 70 hours.

The elastomers utilized in the mixes were the P.1 defined in the preceding examples and the P.40, which is a terpolymer composed for 54.1% by moles of $CH_2=CF_2$, for 22.2% by moles of $C_3F_6$ and for 22.9% of $C_2F_4$, containing bromoperfluoroethylvinylether in an amount equal to 0.6% by weight of bromine. Both the mixes and the cured product were characterized too. The following Tables show the characteristics in

EXAMPLE 17 (COMPARISON TEST)

Curing tests were carried out at 180° C. in a mold, using a mix having the composition indicated in examples 1 to 15, except the peroxide, wherein as a peroxide there was utilized a perketale which, by decomposition, prevailingly formed ethyl radicals and a few methyl radicals ($CH_3-CH_2-/CH_3$.ratio=15:1), having the formula:

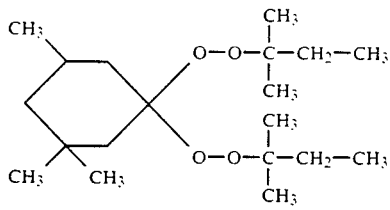

Said peroxide, which was utilized in the mixes in an amount of 1.7 p.h.r., led to a viscosity increase (Δtorque) of only 7 points, against the 67 points obtained by using Luperco 101XL (see Table 1), what indicates that it did not cause the cure of fluoroelastomers at 170°–180° C.

EXAMPLE 18

The peroxide bis(1,1-dimethylpropyl)peroxide (Peroximon S 172) of formula:

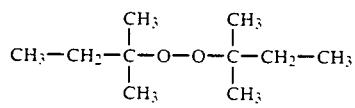

was synthesized.

Into a 4-neck flask of 1 liter of volume, equipped with stirrer, thermometer and an efficient cooler, 400 g of 2-methyl-2-butanol (4.54 moles) were charged.

After having brought the temperature to 40° C., 115.8 g of $H_2O_2$ at 70% (2.383 moles) and 453.4 g of $H_2SO_4$ at 70% (3.236 moles) were simultaneously fed in 60 minutes.

Reaction was stopped after 6 hours by stopping the stirring. After separation, 318.4 g of rough product were obtained (86.5% iodometric titre as peroxide), which was then purified by repeated washings with equal portions of NaOH at 10%. The washed product was then purified by means of rectification under vacuum, thereby obtaining 250 g of product at 99.5% of gas-chromatographic titre.

The obtained product was identified by means of NMR, gas-mass and iodometric analyses.

EXAMPLE 19

The peroxide bis(1,1-diethylpropyl)peroxide (Peroximon S 173) of formula:

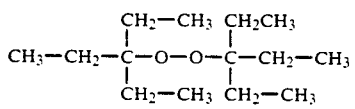

was synthesized.

First step

In a 500 ml flask equipped with stirrer and cooling system, 1 mole of triethylcarbinol was reacted with 2 moles of $H_2O_2$ at 70% in the presence of 1 mole of $H_2SO_4$ in a solvent consisting of 1.3 moles of hexane, at a temperature of 20° C. for a time of 2–4 hours.

On conclusion of the reaction, the organic phase was separated from the aqueous phase and neutralization was carried out with 20 g of a NaOH solution at 1%.

Second step

The organic phase coming from the first step was then additioned with 1 mole of triethylcarbinol, and to the resulting mixture, after evaporation of the solvent at 0° C. under vacuum, 2 moles of paratoluenesulphonic acid as aqueous solution at 70% were added. The reaction mixture was then reacted at 35° C. for 24 hours.

From the reaction mixture, the peroxide was then separated by decantation of the organic phase and subsequently it was purified by means of repeated washings with a NaOH solution at 10%.

After filtration and removal under vacuum of the lighter fractions, a residue was obtained, which consisted of the peroxide bis(1,1-diethylpropyl)peroxide, which was identified by NMR, iodometric and gas-mass analyses.

EXAMPLE 20

The peroxide bis (1-ethyl-1-methylpropyl)peroxide (Peroximon S 176) of formula:

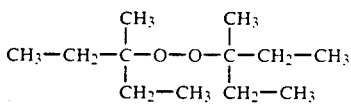

was synthesized.

First step

Into a 4-neck flask having a 0.5 liter volume, equipped with stirrer, thermometer and an efficient cooler, 100 g of 3-methyl-3-pentanol (0.979 moles) were charged. After having brought the temperature to 30° C., 95.1 g of $H_2O_2$ at 70% (1.957 moles) and 137.1 g of $H_2SO_4$ at 70% (0.979 moles) were simultaneously charged in 30 minutes.

The reaction was stopped after 3 hours.

After separation of the phases, 112.8 g of 1-methyl-1-ethylpropyl hydroperoxide at 99% of iodometric titre were obtained.

Second step

Into a 1 liter flask, 112.8 g of hydroperoxide and 100 g of 3-methyl-3-pentanol (0.979 moles) were charged. The whole was brought to 40° C. and 394.5 g of p.toluenesulphonic acid at 70% (1.603 moles) were fed in 20 minutes.

The reaction was stopped after 18 hours and 120.5 g of a rough product were obtained. The rough product was purified by means of repeated washings with NaOH at 20% and then it was rectified under vacuum: there were obtained 95 g of peroxide at 96% of iodometric titre, identified through NMR and gas-mass analyses.

EXAMPLE 21

The peroxide 1,1-diethylpropyl, 1-ethyl-1-methylpropyl-peroxide (Peroximon S 185) of formula:

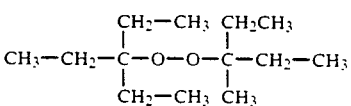

was synthesized.

It was operated in like manner as is described in example 19, with the exception that in the second step diethylcarbinol was utilized instead of triethylcarbinol. The peroxide was characterized by means of NMR, iodometric and gas-mass analyses.

EXAMPLE 22

The peroxide 2,5-dimethyl-2,5-di-ter.amyl-peroxyhexane (Peroximon S 179) of formula:

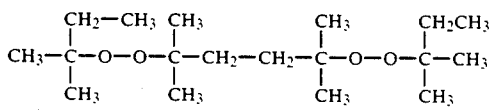

was synthesized.

Into a 4-neck flask having a 1 liter volume, equipped with stirrer, thermometer and an efficient cooler, 176.3 g of 2-methyl-2-butanol (2.0 moles) and 445.7 g of 2,5-dimethyl-2,5-bis(hydroperoxy)hexane at 80% (2 moles) were charged.

While maintaining the temperature at 30° C., 280.3 g of $H_2SO_4$ at 70% (2.0 moles) were then fed in 30 minutes. The reaction was interrupted after 6 hours by stopping stirring and separating the two phases which were formed. The resulting rough product (400 g) was repeatedly washed with NaOH at 10% and with demineralized water in equal amounts.

After rectification under vacuum (residual 11 m of Hg), there were obtained 350 g of product at 90% (gas-chromatographic titre) which, by NMR, gas-mass and iodometric analyses, was identified as 2,5-dimethyl-2,5-bis(ter.amylperoxy)hexane.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Curable mixes based on fluoroelastomers containing bromine and/or iodine in the polymeric chain, comprising organic peroxides as radical cross-linking agents, characterized in that the peroxides are selected from the monoperoxides of formula:

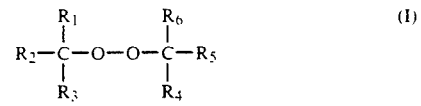

wherein:
$R_1$, $R_6$, like or different from each other, are $C_2$-$C_4$ alkyls;
$R_3$, $R_4$, like or different from each other, are $C_1$-$C_4$ alkyls;
$R_2$, $R_5$, like or different from each other, are $C_1$-$C_4$ alkyls, phenyls, phenyls substituted by $C_1$-$C_4$ alkyls;

and the bisperoxides of formula:

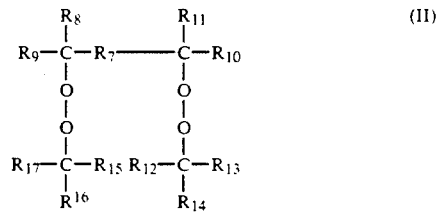

wherein
$R_7$ is $C_1$-$C_6$ alkylene, $C_2$-$C_6$ alkenylene, $C_2$-$C_6$ alkynylene, phenylene;
$R_8$, $R_9$, $R_{10}$, $R_{11}$, like or different from one another, are $C_1$-$C_3$ alkyls;
$R_{13}$, $R_{15}$, like or different from each other, are $C_2$-$C_4$ alkyls;
$R_{12}$, $R_{14}$, $R_{16}$, $R_{17}$, like or different from one another, are $C_1$-$C_4$ alkyls;
provided that, when $R_7$ is phenylene $R_8$, $R_{11}$, like or different from each other, are $C_2$-$C_4$ alkyls.

2. The mixes according to claim 1, wherein the peroxide is bis(1,1-dimethylpropyl)peroxide.

3. The mixes according to claim 1, wherein the peroxide is bis(1,1-diethylpropyl)peroxide.

4. The mixes according to claim 1, wherein the peroxide is bis(1-ethyl-1-methylpropyl)peroxide.

5. The mixes according to claim 1, wherein the peroxide is 1,1-diethylpropyl, 1-ethyl-1-methylpropyl-peroxide.

6. The mixes according to claim 1, wherein the peroxide is 2,5-dimethyl-2,5-di-ter.amylperoxy-hexane.

7. The mixes according to claim 1, furthermore containing from 0.1 to 1 part by weight of benzothiazole or derivatives thereof.

8. The mixes according to claim 1, furthermore containing from 0.1 to 2 parts by weight of N-phenylmaleimide.

* * * * *